(12) United States Patent
Bartal et al.

(10) Patent No.: US 7,894,885 B2
(45) Date of Patent: Feb. 22, 2011

(54) COHERENT SIGNAL REJECTION IN ECG

(75) Inventors: Meir Bartal, Zichron (IL); Daniel Razansky, Brighton, MA (US)

(73) Assignee: Biosense Webster, Inc., Diamond Bar, CA (US)

( * ) Notice: Subject to any disclaimer, the term of this patent is extended or adjusted under 35 U.S.C. 154(b) by 965 days.

(21) Appl. No.: 11/743,195

(22) Filed: May 2, 2007

(65) Prior Publication Data

US 2008/0275353 A1    Nov. 6, 2008

(51) Int. Cl.
*A61B 5/0402* (2006.01)
(52) U.S. Cl. ........................ 600/509; 600/508
(58) Field of Classification Search .................. None
See application file for complete search history.

(56) References Cited

U.S. PATENT DOCUMENTS

| | | | |
|---|---|---|---|
| 4,211,237 A | | 7/1980 | Nagel |
| 4,537,200 A | * | 8/1985 | Widrow ...................... 600/509 |
| 4,887,609 A | | 12/1989 | Cole, Jr. |
| 5,188,117 A | | 2/1993 | Steinhaus et al. |
| 5,349,352 A | | 9/1994 | Saleh |
| 5,564,428 A | | 10/1996 | Soernmo et al. |
| 5,983,127 A | * | 11/1999 | dePinto ....................... 600/509 |
| 6,351,664 B1 | * | 2/2002 | Brodnick ..................... 600/509 |
| 6,807,443 B2 | | 10/2004 | Keren |
| 2007/0083128 A1 | | 4/2007 | Cote et al. |

OTHER PUBLICATIONS

Extended European Search Report re: EP08251600 dated Aug. 14, 2008.

* cited by examiner

*Primary Examiner*—Carl H Layno
*Assistant Examiner*—Paula J Stice
(74) *Attorney, Agent, or Firm*—Louis J. Capezzuto

(57) ABSTRACT

A method for monitoring an electrocardiogram (ECG) signal of a subject, includes digitally sampling an average signal from at least a first ECG electrode, determining an average interference frequency, and digitally sampling and buffering a raw ECG signal from at least a second ECG electrode. The method further includes: filtering the raw ECG signal to generate a residual signal; calculating, based on the residual signal, a first amplitude and a first phase shift of a primary interference signal at the average interference frequency and a second amplitude and a second phase shift of one or more harmonic interference signals at respective multiples of the average interference frequency; and digitally subtracting the primary interference signal and the one or more harmonic interference signals from the raw ECG signal so as to generate and output a clean ECG signal.

6 Claims, 3 Drawing Sheets

COHERENT SIGNAL REJECTION IN ECG

FIELD OF THE INVENTION

The present invention relates generally to monitoring biophysical parameters and in particular to the measurement of ECG signals.

BACKGROUND OF THE INVENTION

Instruments for measuring electrocardiogram (ECG) signals often detect electrical interference corresponding to a line, or mains, frequency. Line frequencies in most countries, though nominally set at 50 Hz or 60 Hz, may vary by several percent from these nominal values.

Various methods for removing electrical interference from ECG signals are known in the art. Several of these methods make use of one or more low-pass or notch filters. For example, U.S. Pat. No. 4,887,609, whose disclosure is incorporated herein by reference, describes a system for variable filtering of noise in ECG signals. The system has a plurality of low pass filters including one filter with a 3 dB point at approximately 50 Hz and a second low pass filter with a 3 dB point at approximately 5 Hz.

U.S. Pat. No. 6,807,443, whose disclosure is incorporated herein by reference, describes a system for rejecting the line frequency component of an ECG signal by passing the signal through two serially linked notch filters. U.S. Pat. No. 5,188,117, whose disclosure is incorporated herein by reference, describes a system with a notch filter that may have either or both low-pass and high-pass coefficients for removing line frequency components from an ECG signal. The system also provides means for removing burst noise and for calculating a heart rate from the notch filter output.

U.S. Pat. No. 5,564,428, whose disclosure is incorporated herein by reference, describes a system with several units for removing interference: a mean value unit to generate an average signal over several cardiac cycles, a subtracting unit to subtract the average signal from the input signal to generate a residual signal, a filter unit to provide a filtered signal from the residual signal, and an addition unit to add the filtered signal to the average signal.

U.S. Pat. No. 5,349,352, whose disclosure is incorporated herein by reference, describes an analog-to-digital (A/D) converter that provides noise rejection by synchronizing a clock of the converter with a phase locked loop set to the line frequency.

SUMMARY OF THE INVENTION

Embodiments of the present invention provide methods and devices for removing electrical interference from a physiological signal. The embodiments described hereinbelow are particularly useful for filtering line interference induced in an electrocardiogram (ECG) signal. The principles of the present invention may also be applied in filtering other types of interference, such as interference induced by magnetic location systems and by magnetic resonance systems.

In certain embodiments, a monitor digitally samples an ECG signal, referred to hereinbelow as a raw ECG signal. The monitor also samples an average signal, such as a signal acquired from a Wilson Central Terminal (WCT). The average signal is processed to determine an average frequency of primary interference.

The raw ECG signal is then processed to remove signals at the average frequency of primary interference and at harmonics of that frequency. The filtered signal is subtracted from the raw signal to generate a residual signal, which includes interference signals at the average frequency and its harmonics. Amplitudes and phase shifts of these interference signals are estimated, artifacts are removed, and the resulting interference signals are subtracted from the raw ECG signal to generate a line-filtered ECG signal.

There is therefore provided, in accordance with an embodiment of the present invention, a method for monitoring an electrocardiogram (ECG) signal of a subject, including:
digitally sampling an average signal from at least a first ECG electrode attached to the subject;
determining an average interference frequency of the average signal;
digitally sampling and buffering a raw ECG signal from at least a second ECG electrode attached to the subject;
filtering the raw ECG signal to generate a residual signal including frequency components at and above the average interference frequency;
calculating, based on the residual signal, a first amplitude and a first phase shift of a primary interference signal at the average interference frequency and a second amplitude and a second phase shift of one or more harmonic interference signals at respective multiples of the average interference frequency; and
digitally subtracting the primary interference signal and the one or more harmonic interference signals from the raw ECG signal so as to generate and output a clean ECG signal.

Typically, the average signal includes a Wilson Central Terminal (WCT) signal.

The method may include imposing a limit on a change in the first amplitude prior to subtracting the primary interference signal from the raw ECG signal. Imposing the limit may include setting the first amplitude equal to a preceding value of the first amplitude, responsively to determining that the first amplitude has changed by more than a predetermined factor relative to the preceding value. Imposing the limit may also include calculating a mean value of the residual signal and calculating a threshold based on the mean value. A limit may also be imposed on a change in the second amplitude prior to subtracting the one or more harmonic interference signals from the raw ECG signal.

In some embodiments, filtering the raw ECG signal includes applying to the raw ECG signal to a moving average filter, and generating the residual signal includes subtracting an output of the moving average filter from the raw ECG signal.

Calculating the first amplitude and the first phase shift may include finding a correlation between the residual signal and a periodic function having a frequency equal to the average interference frequency.

Similarly, calculating the second amplitude and the second phase shift may include finding a correlation between the residual signal and a periodic function having a frequency equal to a multiple of the average interference frequency.

There is also provided, in accordance with an embodiment of the present invention, apparatus for monitoring an electrocardiogram (ECG) signal of a subject, including:
a plurality of ECG electrodes, including at least a first and a second ECG electrode, attached to the subject; and
a processor configured to sample an average signal from at least the first ECG electrode, to determine an average interference frequency of the average signal, to sample and buffer a raw ECG signal from at least the second ECG electrode, to filter the raw ECG signal to generate a residual signal including frequency components at and above the average interference frequency, to calculate, based on the residual signal, a first amplitude and a first phase shift of a primary interference signal at the average interference frequency and a second amplitude and a second phase shift of one or more harmonic interference signals at respective multiples of the average interference frequency, and to subtract the primary interference signal and the one or more harmonic interference signals from the raw ECG signal so as to generate and output a clean ECG signal.

The present invention will be more fully understood from the following detailed description of the embodiments thereof, taken together with the drawings in which:

DETAILED DESCRIPTION OF EMBODIMENTS

Figure 1:
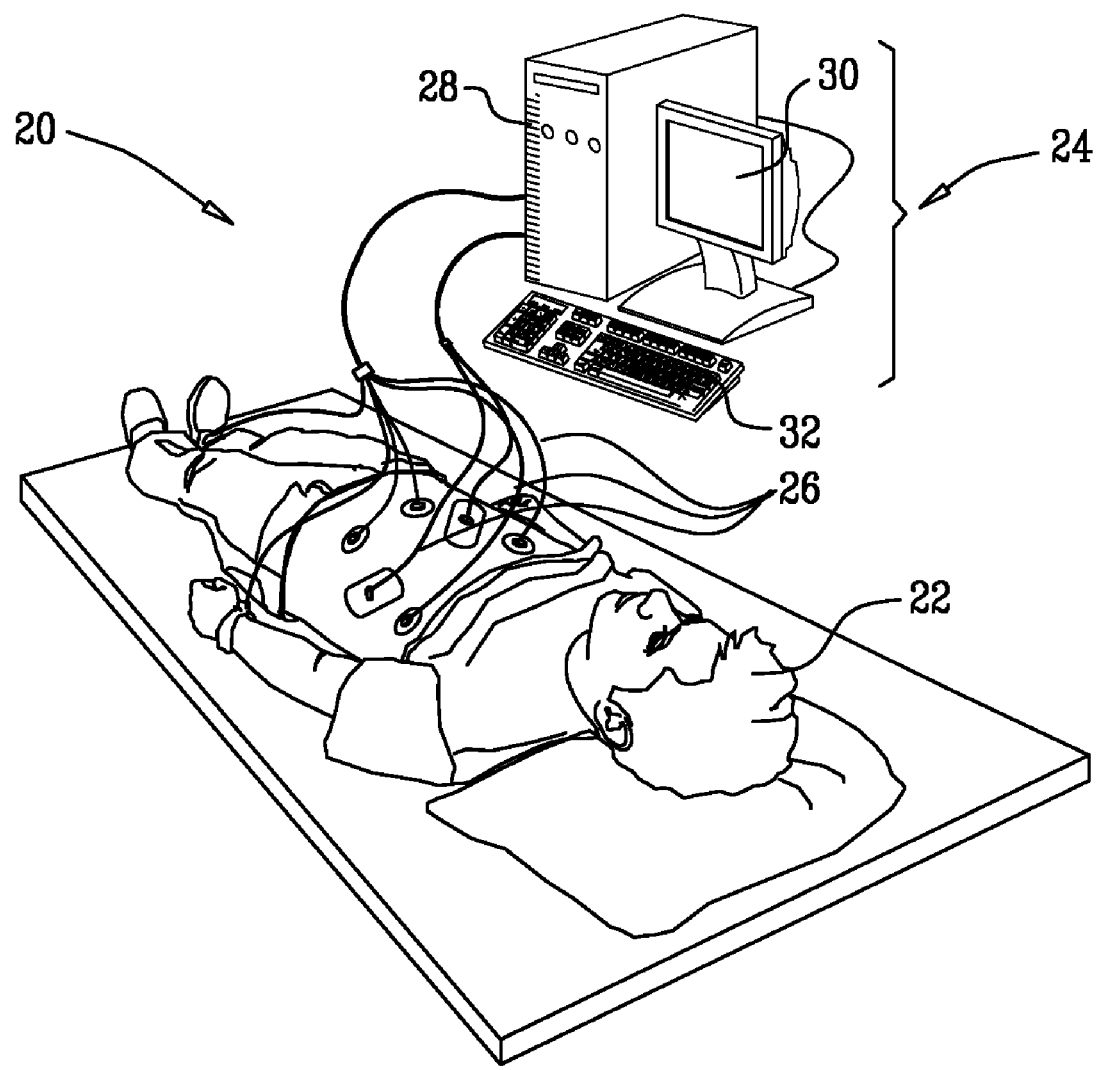
FIG. 1 is a schematic, pictorial illustration of a system for monitoring an ECG signal, in accordance with an embodiment of the present invention.

FIG. 1 is a schematic, pictorial illustration of a system 20 for measuring and processing ECG signals of a patient 22, in accordance with an embodiment of the present invention. ECG signals are acquired by an ECG monitor 24 from electrodes 26 placed on the body of patient 22. ECG monitor 24 comprises an ECG processor 28 that processes the acquired signals and generates filtered signals that are presented on an output device, such as a computer screen 30. Output devices may also include a printer as well as means for remote transmission and storage of the processed signals.

In addition to presenting filtered signals, the ECG monitor may also monitor other physiological parameters, such as ECG signal changes that may indicate heart failure. The ECG monitor may also transmit signals to external systems that provide for presentation, storage, or further signal processing. A user of ECG monitor 24 may modify processing and presentation parameters through an input panel such as a keyboard 32. Presentation parameters may include options to view specific signals, as well as display options such as pan and zoom. Processing parameters may determine the type and extent of signal filtering, as well as settings for artifact thresholds, as described further hereinbelow.

Many configurations for placing electrodes 26 on a patient's body are documented in the prior art. In a common configuration of ten electrodes, cited here by way of example, six of electrodes 26 are placed across the chest of patient 22 and four are placed at the extremities comprising the patient's left arm, right arm, left leg, and right leg. ECG signals are measured across various sets of the ten electrodes. Signals typically measured by the common ten-electrode configuration, are known as signals I, II, III, aVR, aVL, aVF, V1, V2, V3, V4, V5, and V6.

An average of three extremity voltages (by convention, voltages measured at the right arm, left arm, and left leg), is known as the Wilson Central Terminal (WCT). The WCT was initially described in Wilson N F, Johnston F E, Macleod A G, Barker P S, "Electrocardiograms that represent the potential variations of a single electrode," *Am. Heart Journal*, (1934; 9:447-458), whose disclosure is incorporated herein by reference. The WCT is often used as a reference voltage for the V1-V6 signals and is therefore available for additional signal processing.

Line interference that is induced in the body extremities is typically prevalent in the WCT. ECG processor 28 exploits this aspect of the WCT to determine the line interference frequency, as described further hereinbelow.

Figure 2:
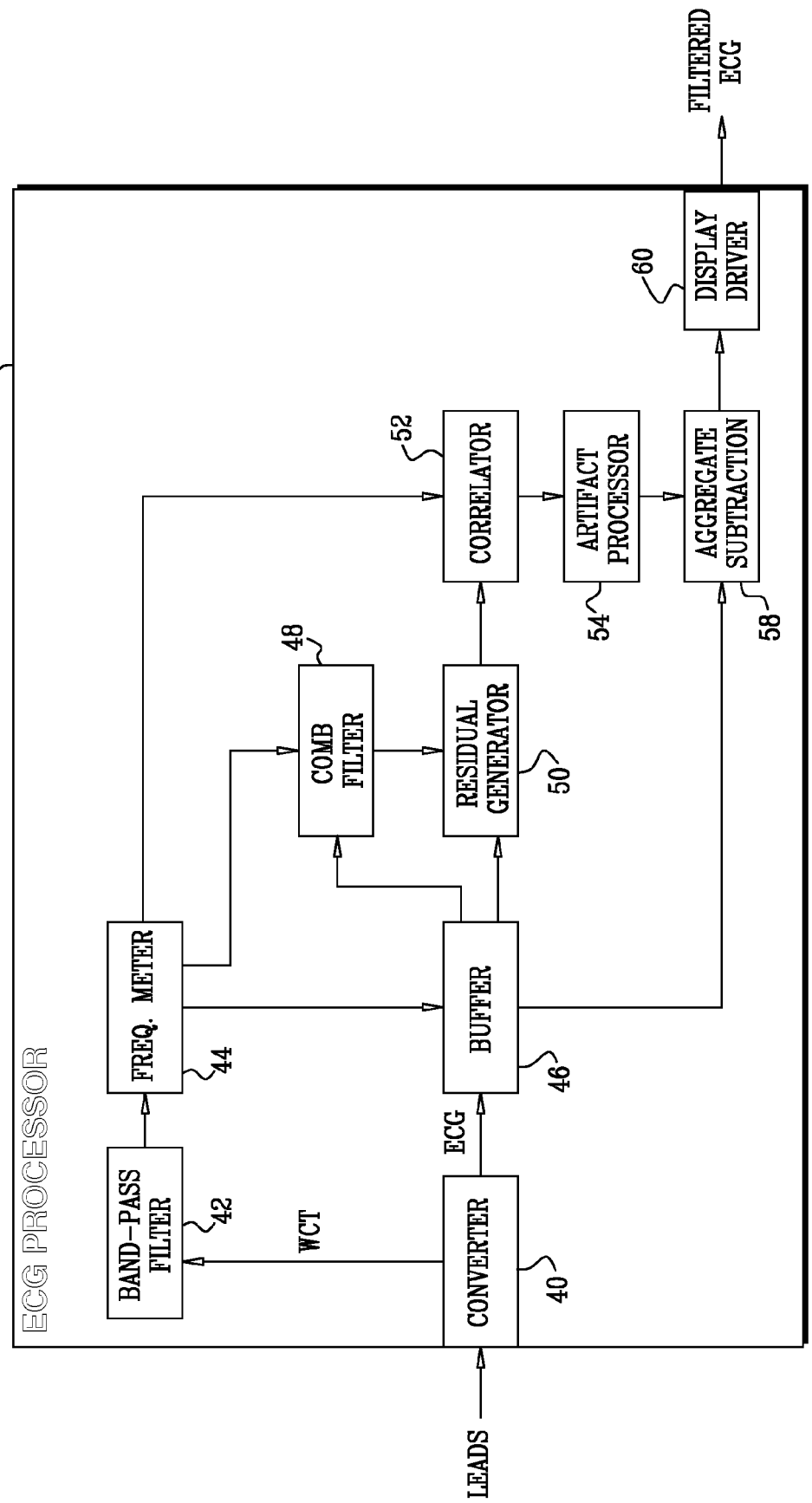
FIG. 2 is a block diagram that schematically shows details of an ECG processor, in accordance with an embodiment of the present invention.

FIG. 2 is a block diagram that schematically shows elements of ECG processor 28, in accordance with an embodiment of the present invention. ECG processor 28 may comprise a general-purpose computer, running any suitable operating system, with suitable input interfaces (not shown) for receiving ECG signals and software for performing the processing functions that are described hereinbelow. This software may be downloaded to the processor in electronic form, over a network, for example, or may be stored on tangible media, such as optical, magnetic, or electronic memory media. Alternatively or additionally, the ECG processor may comprise a special-purpose processing device, such as a programmable signal processor or a customized hardware control unit. Elements of ECG processor 28 may also be implemented as several separate processing devices.

In an embodiment of the present invention, a raw ECG signal, such as the aVR signal, is acquired from electrodes 26 and converted from an analog to a digital format by a converter 40. Converter 40 also acquires and provides a digital output of an average signal, such as the WCT signal. It is desirable that the sampling frequency ($f_s$) of converter 40 be significantly higher than the line frequency ($f_l$) to provide a high level of interference rejection. In certain embodiments, the sampling frequency is set at 8000 samples/sec.

In some embodiments, a band-pass filter 42 then processes the WCT signal to extract signal components in a range that includes the line interference component. A typical band-pass frequency range is set as 45-65 Hz (at −6 db). The band-pass filtered signal is then processed by a frequency meter 44, which determines the frequency of the line interference component. This determination may be made by measuring the time required for a set number of zero voltage crossings of the band-pass filtered signal. In one embodiment, the number of zero crossings counted is set to 120, i.e., 60 cycles. The calculation may also be performed by determining zero crossings of a second derivative of the band-pass signal. An average line interference frequency over the 60 cycles is calculated as $f_l = 60 f_s / N_{60,av}$, wherein $N_{60,av}$ is the number of zero crossings counted. In an embodiment of the present invention, the average line interference frequency is updated on a continuous basis as each digital sample from the WCT is acquired.

Samples, $x_n$, comprising the raw ECG signal acquired by converter 40, are buffered in a frame buffer 46. In some embodiments, frame buffer 46 stores an ECG frame of exactly four cycles of the ECG signal or $N_{60,av}/15$ samples, as calculated by frequency meter 44. The frame length is set to four cycles as a compromise between minimizing processing time and providing sufficient information for the correlation procedure described hereinbelow. The samples are transmitted from frame buffer 46 to a comb filter 48. The comb filter may be implemented as a moving average of the raw signal, wherein the average is taken over a single cycle of the average line interference frequency, that is, over $N_{60,av}/60$ samples. The moving average is equal to a sum of $N_{60,av}/60$ terms, divided by the value of $N_{60,av}/60$.

A residual generator 50 subtracts the moving average from the raw ECG signal to generate a residual signal $s_n$. In mathematic terms, the residual signal $s_n$ equals the raw signal, $x_n$, minus the average of $x_n$ over a cycle (the average being the sum of $x_n$ over a cycle divided by $N_{60,av}/60$), as follows:

$$s_n = x_n - \frac{60}{N_{60,av}} \left( \sum_{m=n-N_{60,av}/120}^{n-1+N_{60,av}/120} x_m \right).$$

Residual signal $s_n$ comprises components of the raw ECG signal at frequencies at and above the average line interference frequency (as determined by frequency meter 44). The processes implemented by low pass filter 48 and residual signal generator 50 may be repeated for harmonics of the line frequency, thereby generating, for each harmonic, m, a harmonic-bound residual signal, $s_n^{(m)}$, comprising components at and above the given harmonic frequency:

$$s_n^{(m)} = x_n - \frac{60 \cdot m}{N_{60,av}} \left( \sum_{i=n-N_{60,av}/(120 \cdot m)}^{n-1+N_{60,av}/(120 \cdot m)} x_i \right)$$

The harmonic-bound residual signals $s_n^{(m)}$ are input to a correlator 52, which determines the amplitude (A) and phase shift ($\phi$) of component interference signals in the harmonic-bound residual signals. The term $s_n^{(1)}$ refers to the primary interference signal, also known as the first harmonic interference signal. A second harmonic interference signal corresponds to $s_n^{(2)}$, and so on. Typically, several harmonic-bound residual signals (between 3 and 15) are calculated and input to correlator 52. Processing by all elements of ECG processor 28 is usually performed in real-time, such that a new value for amplitude and phase shift for each component interference signal is calculated as each ECG frame is acquired.

The operation of correlator 52 may be understood as follows. For analog signals, a correlation between a first signal x, having a component interference signal s of frequency f, and a second signal, comprising a cosine function with a frequency f, is given by:

$$\int_C^{qT} x(t)\cos(2\pi f t) dt \approx \int_0^{qT} s(t)\cos(2\pi f t) dt$$
$$= \int_0^{qT} A\sin(2\pi f t + \varphi)\cos(2\pi f t) dt$$
$$= \frac{A}{2} \int_0^{qT} [\sin(\varphi) + \sin(4\pi f t + \varphi)] dt$$
$$= \frac{AqT}{2} \sin\varphi$$
$$= \frac{Aq}{2f} \sin\varphi.$$

Similarly, a correlation between x and a sine function of frequency f may be calculated as:

$$\int_0^{qT} x(t)\sin(2\pi f t) dt \approx \ldots = \frac{Aq}{2f} \cos\varphi.$$

The two correlations provide simultaneous equations for the calculation of amplitude and phase shift for interference signal s:

$$A\cos\varphi = \frac{2f}{q} \int_0^{qT} s(t)\sin(2\pi f t) dt,$$

and $$A\sin\varphi = \frac{2f}{q} \int_0^{qT} s(t)\cos(2\pi f t) dt.$$

For discrete signals, the above equations for amplitude and phase shift are represented, for any given harmonic m, as follows:

1) $A^{(m)}\sin\varphi^{(m)} = \frac{30}{N_{60,av}} \sum_{n=1}^{N_{60,av}/15} s_n^{(m)}\cos(2\pi m f_i n / f_s)$ 2) $A^{(m)}\cos\varphi^{(m)} = \frac{30}{N_{60,av}} \sum_{n=1}^{N_{60,av}/15} s_n^{(m)}\sin(2\pi m f_i n / f_s)$ wherein the integral over t in the analog equations is represented as a summation over n samples, and t is represented as $n/f_s$.

The above summations are performed over a frame of $N_{60,av}/15$ samples, which is equal to four frequency cycles of each respective component interference signal. The frame length may vary depending the allowable delay of the system. Using a larger frame allows more accurate determination of the amplitude and phase but increases the output delay because more samples need to be accumulated.

After the amplitudes and phase shifts of the interference signal harmonics are calculated, as above, an artifact processor 54 may modify the amplitude values, so as to limit the rate of change of these values with time. The limitation may be applied so as to prevent a sudden change between two sequential amplitude values or a sudden change between an amplitude value of the interference signal and a moving average of the amplitude.

From the correlation equations (1) and (2), above, amplitudes for each harmonic are calculated according to the following equation:

$$[A^{(m)}]^2 = [A^{(m)} \sin \phi^{(m)}]^2 + [A^{(m)} \cos \phi^{(m)}]^2.$$

To determine limits on values of amplitude, artifact processor 54 calculates normalized root-mean-square (RMS) amplitudes $[A^{(m)}]^2$ of residual signals $s_n^{(m)}$, as follows:

$$[A_{RMS}^{(m)}]^2 = \frac{15}{N_{60,av}} \sum_{n=1}^{N_{60,av}/15} [s_n^{(m)}]^2.$$

In some embodiments, for a given value of $[A^{(m)}]^2$ that differs by more than a preset, empirically determined threshold based on the RMS amplitude $[A_{RMS}^{(m)}]^2$, the value of $A^{(m)}$ is replaced by an immediately preceding value of $A^{(m)}$. The limitation ensures that higher frequency components of the ECG signal, such as the peak of the QRS complex, will not affect interference estimation accuracy. The inventors have found that setting the threshold to 21% of the RMS amplitude $[A_{RMS}^{(m)}]^2$ gives good results, but other threshold values may similarly be used. Optionally, the user of ECG monitor 24 may adjust the threshold value.

In alternative embodiments, artifact processor 54 calculates a difference between $A^{(m)}$ and an immediately preceding value of $A^{(m)}$, retaining the immediately preceding value in place of the newer value if the difference between the two is greater than a threshold, such as 10% of the preceding value.

After processing of the interference signal by artifact processor 54, an aggregate subtraction module 58 sums all the harmonics of the interference signal and subtracts the sum from the raw ECG signal, to provide a clean, line-filtered ECG signal, $y_n$:

$$y_n = x_n - \sum_m [A^{(m)}\sin\varphi^{(m)}\cos(2\pi m f_i n / f_s) + A^{(m)}\cos\varphi^{(m)}\sin(2\pi m f_i n / f_s)]$$

wherein m=1, 2, . . . is the harmonic number of the interference signal.

The clean ECG signal, may then be transferred to a display driver 60, which controls the display on screen 30.

Figure 3A:
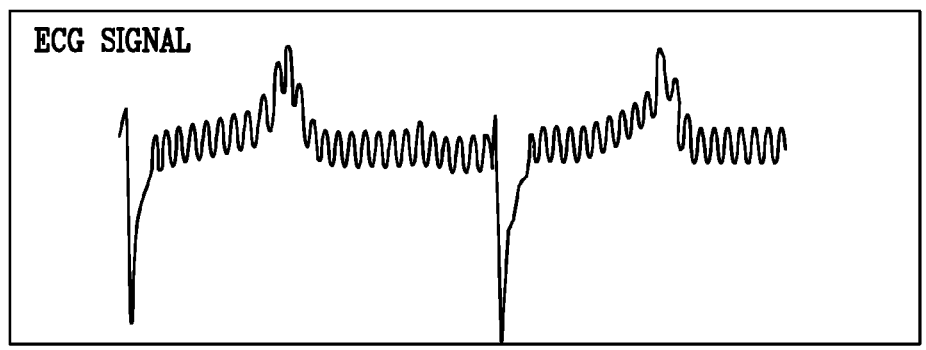
FIGS. 3A-3D are signal diagrams that schematically show ECG signals at four stages of processing, in accordance with embodiments of the present invention.

FIGS. 3A-3D are signal diagrams that schematically show signals at different stages of processing by ECG processor 28, in accordance with embodiments of the present invention. FIG. 3A shows a raw ECG signal, such as an aVR signal. A typical magnitude of this signal is up to several mV, before amplification. It can be seen that the signal includes a substantial interference component.

Figure 3B:
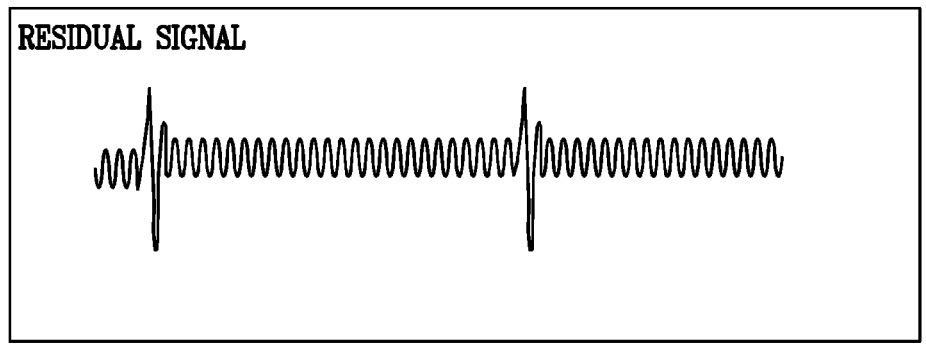

Component interference signals induced on the raw ECG signal are isolated by the methods described hereinabove with respect to FIG. 2. The residual signal produced by residual generator 50 is a precursor to subsequent generation of component interference signals. An example of the residual signal is shown in FIG. 3B. This signal includes not only the interference component, but also high-frequency components of the ECG signal.

Figure 3C:
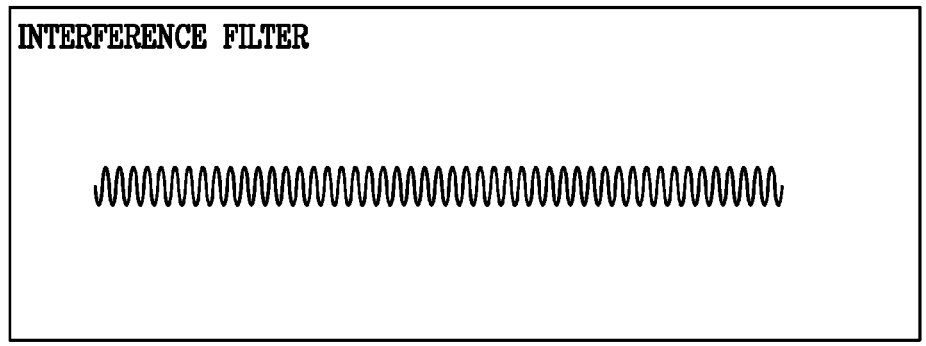
Figure 3D:
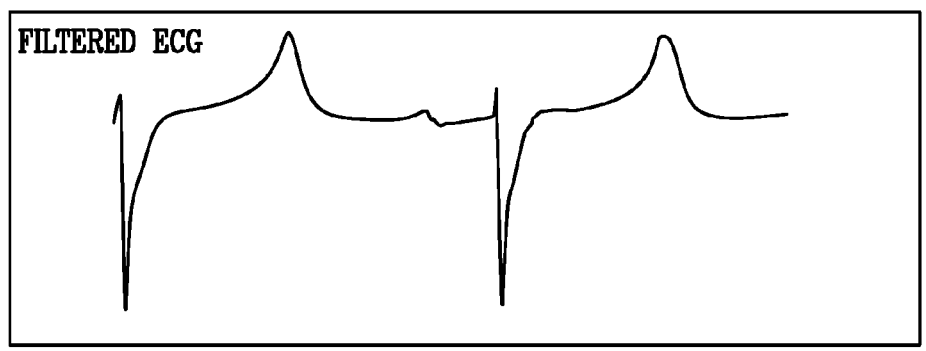

Correlator 52 and artifact processor 54 process the residual signal to generate interference signals correlated to each harmonic of the line interference frequency. FIG. 3C shows an example of an interference signal. Subtracting this component interference signal from the raw ECG signal gives a line-filtered signal, as shown in FIG. 3D.

Although the embodiments described above relate specifically to the removal of line interference from an ECG signal, the principles of the present invention may also be applied to the removal of multiple types of interference from a range of biomedical signals, e.g., EEG, EMG, and various electrically and optically monitored signals. Furthermore, the principles of the present invention may likewise be applied in the context of other environments and industrial applications.

It will thus be appreciated that embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for monitoring an electrocardiogram (ECG) signal of a subject, comprising:

digitally sampling an average signal from ECG electrodes attached to the subject, the average signal comprising a Wilson Central Terminal (WCT) signal;

processing the WCT signal with a band-pass filter to establish a band-pass filter signal, the band-pass filter signal having a line interference component;

processing the band-pass filter signal with a frequency meter and determining a frequency of the line interference component;

determining an average interference frequency of the WCT signal based on the frequency of the line interference component;

digitally sampling and buffering a raw ECG signal from another ECG electrode attached to the subject;

calculating a moving average of the raw ECG signal;

calculating a residual signal using the moving average of the raw ECG signal wherein the residual signal comprises frequency components at and above the average interference frequency;

calculating, based on the residual signal, a first amplitude and a first phase shift of a primary interference signal at the average interference frequency and a second amplitude and a second phase shift of one or more harmonic interference signals at respective multiples of the average interference frequency; and digitally subtracting the primary interference signal and the one or more harmonic interference signals from the raw ECG signal so as to generate and output a clean ECG signal.

2. The method according to claim 1, and comprising using an artifact processor for imposing a limit on a rate of change in the first amplitude over time prior to subtracting the primary interference signal from the raw ECG signal.

3. The method according to claim 2, wherein the limit on the rate of change in the first amplitude over time is a first limit and further comprising imposing a second limit on a rate of change in the second amplitude over time prior to subtracting the one or more harmonic interference signals from the raw ECG signal.

4. The method according to claim 1, wherein filtering the raw ECG signal comprises applying to the raw ECG signal a moving average filter, and wherein generating the residual signal comprises subtracting an output of the moving average filter from the raw ECG signal.

5. The method according to claim 1, wherein calculating the first amplitude and the first phase shift of the primary interference signal comprises finding a correlation between the residual signal and a periodic function having a frequency equal to the average interference frequency.

6. The method according to claim 1, wherein calculating the second amplitude and the second phase shift of the one or more harmonic interference signals comprises finding a correlation between the residual signal and a periodic function having a frequency equal to a multiple of the average interference frequency.

\* \* \* \* \*